United States Patent [19]

Baucom

[11] 4,416,266
[45] Nov. 22, 1983

[54] MEDICAL CLIP

[75] Inventor: Robert M. Baucom, Carrollton, Va.

[73] Assignee: The United States of America as represented by the Administrator of the National Aeronautics and Space Administration, Washington, D.C.

[21] Appl. No.: 264,381

[22] Filed: May 15, 1981

[51] Int. Cl.³ .............................................. A61B 17/12
[52] U.S. Cl. .................................. 128/325; 128/346; 24/560
[58] Field of Search ....... 128/325, 346, 354, DIG. 21, 128/321; 251/9, 10; 24/255 R, 257, 255 BS, 252 R, 254; 267/153; 81/427

[56] References Cited

U.S. PATENT DOCUMENTS

| | | | |
|---|---|---|---|
| 2,519,987 | 8/1950 | Wernette | 24/255 R X |
| 3,604,425 | 9/1971 | LeRoy | 24/255 R X |
| 3,802,437 | 4/1974 | Kees | 128/325 |
| 4,016,883 | 4/1977 | Wright | 128/325 |
| 4,112,951 | 9/1978 | Hulka et al. | 128/346 |
| 4,198,037 | 4/1980 | Anderson | 267/153 |
| 4,274,415 | 6/1981 | Kanamoto et al. | 128/325 X |

FOREIGN PATENT DOCUMENTS 636307  3/1962  Italy ................................. 128/346

OTHER PUBLICATIONS

Todd et al., "Plastic Jackets for Certain Intra-cranial Aneurysms", *The Bulletin* vol. 4, No. 3, Jul. 1962.

*Primary Examiner*—Michael H. Thaler
*Attorney, Agent, or Firm*—Howard J. Osborn; John R. Manning; Wallace J. Nelson

[57] ABSTRACT

An X-ray transparent and biological inert medical clip for treating aneurisms and the like and process for producing same wherein a graphite reinforced composite film 15, 16, 20 and 21 (FIGS. 1a–1d) is molded into a unitary structure having a pair of "hourglass" like cavities 30, 31 (FIG. 2) hinged together (33) with a pair of jaws 27 and 28 for grasping the aneurism extending from the wall of one cavity and a silicone rubber pellet 35 (FIG. 3) disposed in the other cavity to exert a spring force through the hinge area 33 to normally bias the jaws into contact with each other.

3 Claims, 7 Drawing Figures

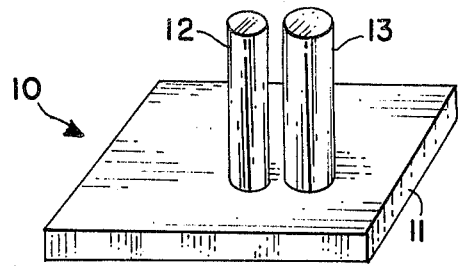

FIG. 1a

PROVIDE MOLD CONSTRUCTED OF TWO STEEL PINS FIXED IN A STEEL BLOCK.

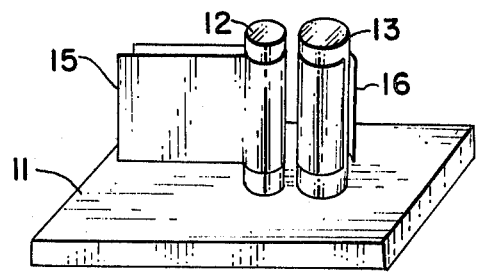

FIG. 1b

WRAP SINGLE PLY OF COMPOSITE FILM AROUND EACH PIN.

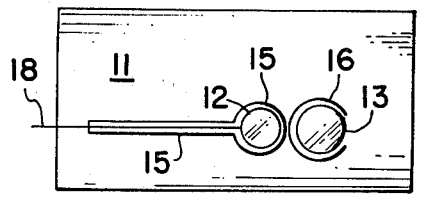

FIG. 1c

INERT SEPARATOR FILM POSITIONED BETWEEN FILM PLY EXTENSIONS.

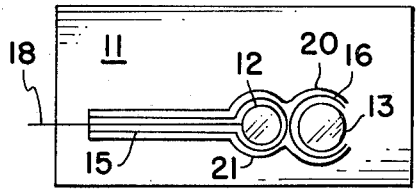

FIG. 1d

ADDITIONAL COMPOSITE PLY OR PLIES ARE PLACED OVER THE FIRST PLIES;

VACUUM BAG, AUTOCLAVE AT ~300 PSI PRESSURE AND 600°F FOR ~30 MINUTES TO CURE THE COMPOSITE MATERIAL. THE ANEURISM CLIP IS THEN REMOVED AND TRIMMED TO DESIRED SIZE.

MEDICAL CLIP

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

In the treatment of aneurisms in man or other living animals, it is accepted practice to utilize a clip implanted at the base of the aneurism to impede further blood flow into the aneurism and permit surgical repair thereof. Present state of the art aneurism clips are normally formed of stainless steel. In many surgical situations the stainless steel clip is installed in a position that is likely to be in the path of subsequent X-ray examination. For typical X-ray films, exposure times, focal distances, and intensities that are utilized in radiography of the human body, stainless steel is opaque to the transmission of X-rays. Thus, dependent upon the position of implanted stainless steel clips, some of the area under X-ray examination can be masked from view by the X-ray characteristic of stainless steel. There is a definite need in the art for X-ray transparent clips that are suitable for implanting in living animals.

It is therefore an object of the present invention to provide a new and improved aneurism clip structure.

Another object of the present invention is the provision of an aneurism clip that is transparent to X-rays.

A further object of the present invention is a novel medical clip that is biologically inert and transparent to X-ray scans.

Another object of the present invention is a novel process for making an X-ray transparent medical clip.

According to the present invention, the foregoing and additional objects are attained by constructing a unitary clip structure from a composite material with the clip having two hourglass type cavities separated by an integral hinge area, one of the cavity walls terminating in spaced ends essentially diametrically opposed to the hinge area and the other of the cavity walls terminating in elongated ends directed away from the cavities and also essentially diametrically opposed to the position of the hinge area. The cavity wall having the spaced end members receives a silicone rubber pellet or disc of adequate circumference to exert a force through the hinge area and maintain the elongated ends extending from the other cavity wall in biased contact to thereby enable use of the assembly as a spring biased clip.

BRIEF DESCRIPTION OF THE DRAWINGS

A more complete appreciation of the invention and many of the attendant advantages thereof will be more readily apparent as the same becomes better understood by reference to the following detailed description when considered in connection with the accompanying drawings wherein:

FIGS. 1a–1d illustrate a schematic flow sheet representing one process for making the basic medical clip according to the present invention;

DETAILED DESCRIPTION OF THE INVENTION

Figure 2:
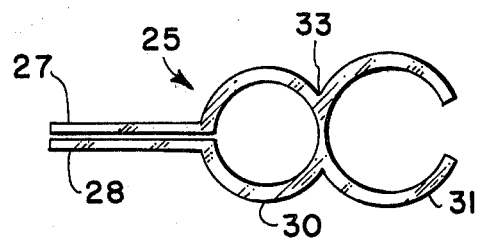
FIG. 2 is a view of the basic medical clip prepared by the process represented in the flow sheet of FIGS. 1a–1d.

Referring now to the drawings and more particularly to FIGS. 1a–1d, a mold 10 of stainless steel or the like is provided in the form of block 11 and two essentially identical spaced cylinders or pins 12 and 13 integrally attached and vertically extending therefrom. In a specific example, pins 12 and 13 were of one-inch length and three-sixteenths and one-quarter inch diameter, respectively, and spaced approximately one-thirty-second inch from each other. Pins of identical diameter have also been used and clips molded thereon perform equally as well as the specific embodiment described herein.

Two lengths (15 and 16) of graphite reinforced polysulfone composite film, as received from the manufacturer, are wrapped separately around pins 12 and 13.

Film thicknesses of from 0.006 to 0.010 inch and widths from fractional to several inches are available and considered applicable for practice of the present invention. The graphite reinforced polysulfone employed in the specific examples herein was obtained from U.S. Polymeric, Inc., 700 E. Dyer Road, Santa Ana, California and identified as "Celion 6K graphite fiber reinforced P1700 polysulfone resin". Any conventional reinforced thermoplastic or thermosetting composite film material that molds or cures into a rigid structure and possesses the physical property characteristics of being biologically inert, able to withstand conventional sterilization procedures and remain transparent to X-rays is considered applicable for practice of the present invention.

As shown in FIGS. 1b and 1c, the length 15 wrapped around pin 12 is of adequate length to provide an elongated extension (approximately one inch) therefrom that is directed away from cylinders 12 and 13. An inert spacer or separator film 18 (Teflon or equivalent inert film) is positioned between the elongated ends of film layer 15 to prevent adherance of the ends as shown in FIG. 1c and as will be further explained hereinafter. The length 16 of the graphite/polysulfone wrapped around pin 13 is trimmed so as to leave a spacing between the film ends with this spacing being diametrically opposed to the extension formed by ply 15 around pin 12.

A second layer or ply 20 and 21 of the same graphite/polysulfone composite film is positioned in abutting relationship with the ends of layers 15 and 16 and the intermediate portion thereof following the contour of pins 12 and 13 but not passing therebetween as shown in FIG. 1d. Additional plies may be placed over film layers 20 and 21 if a more substantial clip structure is desired although in most instances only one layer 20 and 21 is needed or desired. This structure is then placed in a conventional vacuum bag assembly and autoclaved at approximately 300 psi pressure and 600° F. temperature for approximately 30 minutes to effect molding of the graphite/polysulfone. After molding, the assembly is cooled and the clip structure recovered is as illustrated in FIG. 2 and generally designated by reference numeral 25.

Clip 25 as shown in FIG. 2 has been stripped from mold pins 12 and 13 and separator film 18 removed from the elongated segments to provide a pair of jaws 27 and 28 integrally connected to structure forming a pair of circular or hourglass shape cavities as designated by reference numerals 30 and 31 and integrally connected at a hinge area 33. Mechanical trimming of clip 25 is effected at this point if needed and to provide the desired size of the clip. In the specific embodiment described herein, the composite stock film employed for constructing clip 25 had a width of one inch. Since the clip structure normally used is only required to be one-eighth to one-quarter inch wide, the clip structure formed by the above described process was longitudinally cut into four equal width individual clip members by a band saw. After cutting, the cut edges were filed in a conventional manner to achieve smooth surface areas prior to insertion of the silicone rubber "spring". As shown in the drawings the wall of structure 31 forming one of the cavities is formed with spaced ends to provide an opening (not designated) at an area diametrically opposed to the location of jaws 27 and 28.

Figure 3:
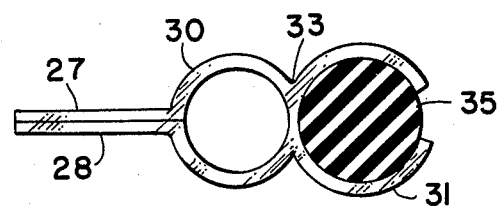
FIG. 3 is a view of the medical clip shown in FIG. 2 with the spring biasing silicone rubber pellet installed.

Referring now to FIG. 3, a silicone rubber pellet or disc 35 of slightly larger diameter than the cavity formed by wall 31 is positioned therein to provide a spring force on the jaws 27 and 28 of clip 25 through hinge area 33 and thereby maintain jaws 27 and 28 in biased contact with each other. Silicone rubber disc 35 is constructed of commercially available silicone rubber and is trimmed so as to be essentially equal to the width of clip 25. In the specific example described herein, the silicone rubber "spring" was cut from a standard "0"-ring seal of five-sixteenths inch diameter and stretched to reduce the diameter thereof sufficiently to be received by cavity 31. When the stretched silicone disc was released it expanded to fill cavity 31 and exert the necessary spring force on clip 25. The molded clip 25 has the inherent physical property characteristic of being resilient and silicone rubber disc 35 exerts adequate spring force through hinge area 33 to provide a reliable clip force on jaws 27 and 28 to serve as an aneurism clip or the like.

Figure 4:
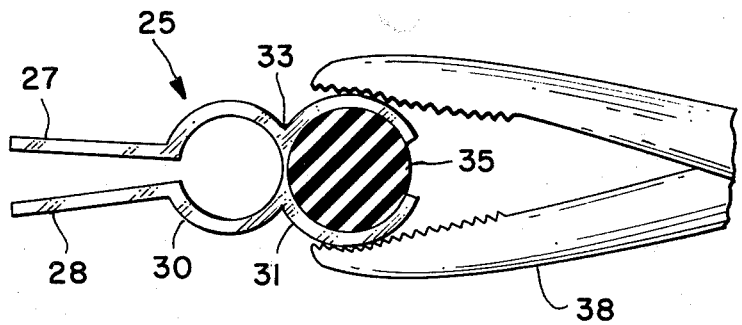
FIG. 4 is an illustration of how the complete medical clip shown in FIG. 3 is opened for implantation by the surgeon.

As shown in FIG. 4 when the surgeon is ready to implant clip 25 into a living animal (after sterilization of the clip by conventional procedures) the wall 31 is grasped by surgical instrument 38 to exert a squeezing force thereon to spread jaws 27 and 28 adequately for positioning around the base of the aneurism. Upon removal of instrument 38, silicone ball 35 exerts a spring force through hinge area 33 and jaws 27 and 28 close to tightly clamp the base of the aneurism as with the currently used stainless steel clips.

It is thus seen that the present invention provides a new and novel medical clip and process for producing same that is biologically inert while being transparent to X-ray examination of the living animal in which the clip may be implanted.

Although the invention has been described relative to a specific embodiment thereof, it is not so limited and numerous modifications and variations thereof will be readily apparent to those skilled in the art in the light of the above teachings. For example, although a specific composite material has been described for constructing the basic clip, the invention is not so limited and any composite or biologically inert and X-ray transparent material that will withstand sterilization procedures and can be fabricated as described herein to produce a resilient clip is considered within the scope of the present invention. For example, although the specific example utilizes graphite fiber reinforced polysulfone, other fibers and other matrix resins are not excluded and are considered within the scope of the present invention as defined in the appended claims. Also, the spring force material is not to be limited to silicone rubber pellets and any spring force producing material that meets the criteria of being biologically inert, transparent to X-ray examinations and adapted to withstand sterilization procedures is considered within the scope of this invention.

Thus, the invention may be practiced other than as described herein without departing from the spirit and scope of the appended claims.

What is claimed as new and desired to be secured by Letters Patent of the United States is:

1. A medical clip for use in treating aneurisms and the like in a living animal and having the inherent physical property characteristic of being essentially transparent to X-rays, comprising:

a unitary structure terminating at one end with a pair of elongated jaws having essentially flat abutting surfaces and the other end with a broken circular segment;

an intermediate segment integrally disposed between said elongated jaws and said broken circular end and formed of a pair of semicircular portions extending from said elongated jaws;

a connection area between the said pair of semicircular portions and said broken circular segment and disposed substantially 180° relative to said elongated jaws;

means provided on said connection area serving as a hinge connection for said unitary structure so as to permit opening and closing of said pair of elongated jaws;

said hinge connection joining said broken circular segment and said intermediate segment to form a pair of "hourglass" cavities;

a silicone rubber insert being disposed within the cavity formed by said broken circle segment to serve as a spring force to pivotally contract said elongated jaws against each other through said hinge connection; and said unitary structure being formed of a molded composite material having the inherent physical property characteristic of being biologically inert, transparent to X-rays and capable of withstanding conventional sterilization procedures.

2. The medical clip of claim 1 wherein said molded composite structure is constructed from plies of graphite fiber reinforced polysulfone film.

3. The medical clip of claim 1 wherein said graphite fiber reinforced polysulfone film is of a thickness range of 0.006 to 0.010 inch and at least two ply thickness of said film is provided in all areas of the clip structure.

* * * * *